United States Patent [19]

Collins et al.

[11] Patent Number: 4,499,296
[45] Date of Patent: Feb. 12, 1985

[54] OMEGA CYCLOALKYL PROSTAGLANDINS

[75] Inventors: Paul W. Collins, Deerfield; Alan F. Gasiecki, Vernon Hills, both of Ill.

[73] Assignee: G. D. Searle & Co., Skokie, Ill.

[21] Appl. No.: 551,238

[22] Filed: Nov. 14, 1983

[51] Int. Cl.³ .................. C07C 177/00; A61K 31/557
[52] U.S. Cl. .................................... 560/118; 562/500; 568/367
[58] Field of Search ....................... 560/118; 562/500; 568/367

[56] References Cited

U.S. PATENT DOCUMENTS

| | | | |
|---|---|---|---|
| 3,965,143 | 6/1976 | Collins | 560/121 |
| 4,271,314 | 6/1981 | Collins | 560/121 |
| 4,275,224 | 6/1981 | Kluender | 560/116 |
| 4,281,153 | 7/1981 | Floyd | 560/118 |

Primary Examiner—Robert Gerstl
Attorney, Agent, or Firm—John J. McDonnell

[57] ABSTRACT

This invention encompasses prostaglandins of the formula I

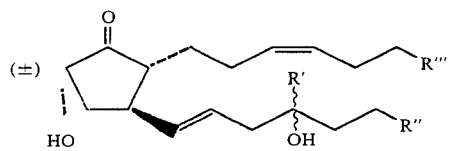

wherein R''' represents hydroxymethyl, hydroxyacetyl or —$CO_2R''''$ wherein R'''' represents hydrogen or lower alkyl containing 1 to 6 carbon atoms;
  R' represents lower alkyl containing 1 to 6 carbon atoms, vinyl or ethynyl;
  R" represents cycloalkyl containing 3 to 5 carbon atoms; and the wavy line represents optional R,S stereochemistry.

These compounds are potent antisecretory compounds and cytoprotective agents with reduced diarrhea side effects.

6 Claims, No Drawings

OMEGA CYCLOALKYL PROSTAGLANDINS

BACKGROUND OF THE INVENTION

U.S. Pat. No. 3,965,143 generally describes compounds of the formula

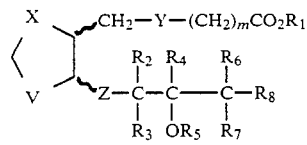

wherein $R_1$, $R_2$, $R_3$, $R_4$, $R_6$ and $R_7$ can be hydrogen or a lower alkyl radical, $R_5$ can be hydrogen or a lower alkanoyl, tetrahydrofuranyl, tetrahydropyran-2yl, tri(-lower alkyl)silyl or lower alkyl radical, X is a carbonyl, hydroxymethylene or (lower alkanoyl)oxymethylene radical, V is a methylene, hydroxymethylene, (lower alkanoyl)oxymethylene, tetrahydrofuranyloxymethylene, tetrahydropyran-2-yloxymethylene or tri-(lower alkyl)silyloxymethylene radical, Y is an ethylene, cis vinylene or trans-vinylene group, Z is an ethylene, cis vinylene, trans-vinylene or ethynylene radical, the wavy lines denote the alternative α and β stereochemical configurations, the dotted line indicates an optional double bond, m is an integer greater than 2 and less than 5 and $R_8$ is an alkyl group containing 3–5 carbon atoms or cycloalkyl group containing 5–7 carbon atoms. and specifically describes methyl 7-[3(R)-hydroxy-2β-(4(RS)-4-cyclohexylmethyl-4-hydroxy-4-methyl-trans-1-butenyl)-5-oxocyclopentane]-1α-heptanoate, a compound of the formula.

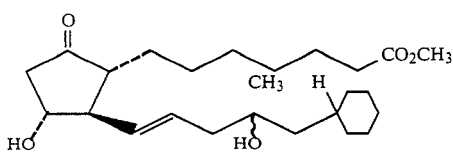

British Pat. No. 1,492,426 describes compounds of the structural formula.

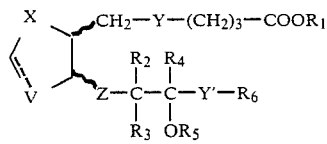

wherein $R_1$, $R_2$, and $R_3$ are hydrogen or an alkyl radical containing from 1 to 7 carbon atoms; $R_4$ is an alkyl radical containing from 1 to 7 carbon atoms; $R_5$ is hydrogen, an alkyl radical containing from 1 to 7 carbon atoms or an alkanoyl radical containing from 1 to 7 carbon atoms; $R_6$ is an alkyl radical containing from 2 to 4 carbon atoms or a cycloaklyl radical containing from 5 to 7 carbon atoms; X is carbonyl or hydroxymethylene; V is methylene, hydroxymethylene or alkanoyloxymethylene wherein the alkanoyl radical contains from 1 to 7 carbon atoms; or when X is carbonyl; V may also be a radical of the formula

in which the bond represented by the dotted line in the general formula is present; Y is ethylene or vinylene; Y' is vinylene, ethynylene or the group

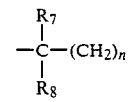

wherein n is 0 to 1 and $R_7$ and $R_8$ are hydrogen or an alkyl radical containing from 1 to 7 carbon atoms; Z is ethylene, vinylene or ethynylene; and the wavy lines represent the alternative α or β stereochemical configuration or the epimeric mixture:

The alkyl radicals represented in the foregoing structural formula are illustrated by methyl, ethyl, propyl, butyl, pentyl, hexyl, heptyl and branched-chain isomers thereof.

The alkanoyl radicals designated in the foregoing formula are exemplified by formyl, acetyl, propionyl, butyryl, valeryl, hexanoyl, heptanoyl, and the corresponding branched-chain isomers.

The cycloalkyl groups designated in the foregoing formula are exemplified by cyclopentyl and cyclohexyl.

Compounds of this invention differ structurally in that they have a cis vinylene radical at the 4–5 postions.

BRIEF DESCRIPTION OF THE INVENTION

The invention encompasses compounds of the formula I

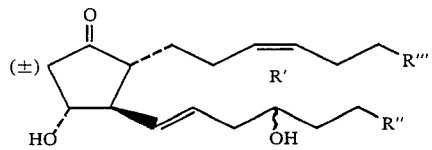

wherein R''' represents hydroxymethyl, hydroxyacetyl or —CO$_2$R''''
wherein R'''' represents hydrogen or lower alkyl containing 1 to 6 carbon atoms;
R' represents lower alkyl containing 1 to 6 carbon atoms, vinyl or ethynyl;
R'' represents cycloalkyl containing 3 to 5 carbon atoms; and the wave line represents optional R,S stereochemistry.

This invention encompasses compounds of the formula I. R''' represents —CH$_2$—OH, —CO—CH$_2$OH, or —CO$_2$R'''' wherein R'''' is hydrogen or lower alkyl such as methyl, ethyl, propyl, isopropyl, butyl, pentyl, or hexyl; R' represents lower alkyl as above as well as vinyl and ethynyl; and R'' represents cycloalkyl such as cyclopropyl, cyclobutyl, or cyclopentyl. These compounds are potent antisecretory and cytoprotective agents with reduced diarrhea side-effects.

DETAILED DESCRIPTION OF THE INVENTION

Compounds of this invention are prepared by the following reaction scheme

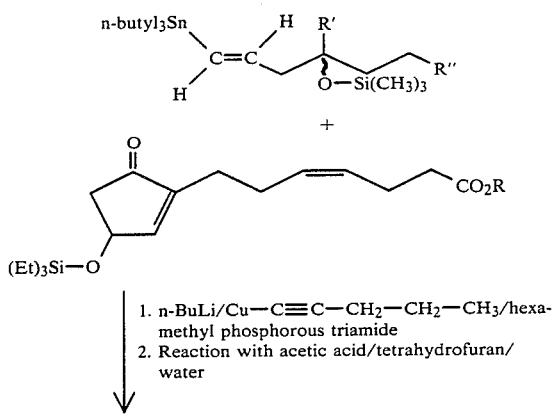

1. n-BuLi/Cu—C≡C—CH₂—CH₂—CH₃/hexamethyl phosphorous triamide
2. Reaction with acetic acid/tetrahydrofuran/water Compounds of Formula I Where R'''=—CO₂R''''

The general reaction is described in U.S. Pat. Nos. 4,322,543 and 4,271,314. These patents also describe methods for varying R from hydrogen, methyl, ethyl, isopropyl butyl and the like as well as varying R' from methyl, ethyl, propyl, isopropyl, vinyl, ethynyl and the like. The latter is for instance accomplished by initiating example 1 of this invention with 6-hepten-3-one to provide a compound of Formula I where R' is ethyl or using vinyl magnesium bromide in place of methyl magnesium bromide in example 2 to provide a compound of Formula I where R' is vinyl.

Methyl 7-[3α-hydroxy-2B-4-hydroxy-4-methyl-6-cyclopentyl-1-trans-hexenyl)-5-oxocyclopentane]1α-hept-4-cis-enoate, the compound prepared in example 2 is the preferred embodiment of this invention by virtue of its potent antisecretory activity and low diarrheogenic properties. The cytoprotective properties of these compounds make them useful in treating ulcers, pancreatitis, and liver disease such as cirrhosis.

Regardless of the route of administration selected, the novel compounds of the invention are formulated into pharmaceutically acceptable dosage forms by conventional methods known to the pharmaceutical art.

The compounds can be administered in such oral unit dosage forms as tablets, capsules, pills, powders, or granules. They also may be administered intraperitoneally, subcutaneously, or intramuscularly, using forms known in the pharmaceutical art. In general, the preferred form of administration is oral. An effective but not-toxic quantity of the compound is employed in treatment. The dosage regimen for cytoprotection by the compounds of this invention is selected in accordance with a variety of factors including the type, age, weight, sex, and medical condition of the patient, the organ to be protected, the route of administration and the particular compound employed. An ordinarily skilled physician will readily determine and prescribe the effective amount of the cytoprotective agent required to prevent or arrest the progress of the condition. In so proceeding, the physician could employ relatively low dosages at first, subsequently increasing the dose until a maximum response is obtained. Dosages of the compounds of the invention are ordinarily in the area of 0.01 to 10,000 ug/kg.

The cytoprotective utility of compounds of this invention are illustrated by standard test which show their ability to reduce ethanol-induced gastric lesions.

0.5 mg/kg is orally administered to adult 180–220 gram mole Charles River rats which have been deprived of food for 24 hours. Thirty minutes later 1.0 ml of absolute ethanol is administered intragastrically. The rats are sacrificed sixty minutes after alcohol administration and the gastric mucosae are visually examined for the presence of lesions. The number and severity of lesions are scored. A compound is judged active if it provides a statistically significant reduction in the number and/or severity of lesions compared to the control group.

The standard test used to detect gastric antisecretory activity is described as follows.

Adult female beagle dogs weighing 6–11 kg. are prepared with whole stomach simple Thomas-type gastric cannulas.

Following full recovery from the surgical implantation of the gastric cannula, the dogs are trained to stand quietly, though fully conscious, in Pavlov-type dog restraining slings and are accustomed to intravenous histamine infusion.

Experiments are initiated by depriving dogs of food, but not water, for 18 hours. With an initial infusion of 0.15M sodium chloride, at a constant rate of 6.5 ml/hr, gastric secretions collected in plastic bottles affixed to the cannula, are taken at 15 minute intervals and measured for volume to the nearest 0.1 ml. Following a 30–45 minute basal secretion period, the collection bottles are removed, dosing plugs inserted, and compound administered. A 3.0 ml saline wash follows immediately.

After the end of a 30 minute drug absorption period the stomachs are emptied, collection bottles again attached, and the collections resumed at 30 minute intervals. Simultaneously, the saline infusion is replaced with a continuous intravenous infusion of histamine dihydrochloride in saline at 15 ug/kg/hr for four hours. Gastric samples are analysed for pH and titratable acidity determinations.

An analysis of the data for each measured or derived variable compares observations recorded following treatment with variables obtained for the same group of animals receiving histamine stimulation alone. Three parameters, gastric juice volume (ml/30 min), acid concentration (mEq/L), and total acid output (mEq/30 min) are analyzed individually. The data thus obtained are analyzed using interval-by-interval paired Student's t-test or two-way analysis of variance to achieve an indication of potency and duration of action. Percentage inhibition is calculated using pooled mean values for the four hour treatment period. Duration of activity is defined as the length of time of significant inhibition.

Diarrhea is an undesirable side effect commonly associated with antisecretory and cytoprotective prostaglandins. Diarrheogenic activity is demonstrated by the following standardized test. Groups of six adult male Charles River rats, weight range 180 to 200 grams, are fasted for 24 hours prior to administering the test substance. The prostaglandin to be tested is administered intragastrically in iso-osmotic phosphate buffer at a volume of 10 ml/kg at doses ranging from 100 to 3000 microgram/kg. Control animals receive only the vehicle. The rats are placed in individual wire mesh cages and the trays lined with brown paper. Diarrhea is assessed at hourly intervals on an all or none basis for up to eight hours after administration of the prostaglandin. Diarrhea is defined as any loose or watery stool. ED₅₀ values are assessed for each hourly diarrheogenic response.

The Compound of Example 2 and formula II

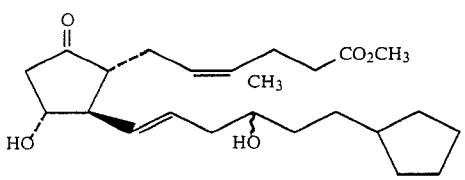

differ only by the position of the double bond i.e. C—5,6 in II and C—4,5 in Example 2, the former falling in the scope of the generic disclosure of British Pat. No. 1,492,468.

These compounds have unexpected differences in antisecretory activity as illustrated by the following data.

Dog Antisecretory $ED_{50}$ ug/kg—Intragastric Administration

| | |
|---|---|
| Compound Example 1 | 0.2 |
| Compound Example 2 | 0.3 |
| versus | |
| Compound II (Prior Art) Inactive at 0.3 and 1.0 | |

The invention is more fully described in the following examples. The examples are not intended to limit the invention in spirit or scope.

EXAMPLE 1

4.9 parts of 5-hexen-2-one is dissolved in 357 parts by volume of benzene under argon and 75 parts by volume of a 25% solution of diethyl zinc is added dropwise over 15 minutes. 40 parts of diiodomethane in 500 parts by volume of benzene is added over 15 minutes. After sitting for 12 hours the reaction mixture is poured into a mixture of hexane and 1N hydrochloric acid. The reaction mixture is extracted several additional times with hexane and the combined organic extracts are washed 3 times with water and once with saturated sodium chloride solution and dried over sodium sulfate, filtered and evaporated. The residual oil is distilled to provide 4-cyclopropyl-2-butanone b.p. 57°–60° C.

To 1 part by volume of magnesium in 25 parts by volume of tetrahydrofuran under argon is added a small amount of propargyl bromide and mercuric chloride to initiate reaction. Once the reaction is started 6.3 parts of propargyl bromide and 36 parts of 4-cyclopropyl-2-butanone in 50 parts by volume of tetrahydrofuran is added dropwise so as to maintain reflux. Upon completion of the reaction, the reaction mixture is cooled to room temperature and poured into a mixture of ether and 1N HCl. The aqueous layer is extracted twice with ether. The ether extracts are combined and washed 3 times with water and one time with saturated sodium chloride solution, dried over anhydrous sodium sulfate, filtered, and evaporated to provide a residual oil. The residual oil is distilled under high vacuum to provide 4-methyl-4-hydroxy-6-cyclopropyl-hex-1-yne.

To a solution of 1,1 part of this material in 10 parts by volume of dimethylformamide containing 1 part of imidazole is added 0.865 parts of trimethylsilyl chloride. After 30 minutes of stirring, the reaction mixture is poured into an ether/water mixture, extracted with more ether and the organic layers are combined and washed with water and saturated sodium chloride solution. The solvent is removed and the residual oil is chromatographed on 5% ethyl acetate/hexane to provide 4-methyl-4-trimethylsilyloxy-6-cyclopropyl-hex-1-yne. 0.577 parts of this material is reacted with 0.748 parts of tri-n-butyl tin hydride at 20° C. catalyzed with ultraviolet light to provide a compound of the formula

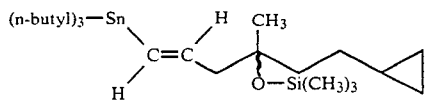

Following the procedures described in U.S. Pat. No. 4,271,314.

0.483 Parts of this trans vinyl tin product is dissolved in 3 parts by volume of tetrahydrofuran cooled to −60° C. and 0.55 parts by volume of 1.66 molar butyl lithium is added while maintaining the reaction mixture in an argon atmosphere. After 1 hour at −60° C. a solution of 0.125 parts of copper pentyne and 0.307 parts of hexamethylphosphorous triamide in 3.5 parts by volume of ether are added. After 10 minutes a solution of 0.176 parts of 7-(3-triethylsilyloxy-5-oxocyclopent-1-ene)-hept-4-cis-enoate (U.S. Pat. No. 4,271,314) in 3.5 parts by volume of ether are slowly added. The solution is stirred for one hour and poured into a mixture of ether and 1N hydrochloric acid. The ether layer is separated, washed twice with water, filtered, dried over sodium sulfate and the ether is removed by evaporation at reduced pressure. The residual oil is chromatographed on silica gel (5% ethyl acetate/hexane as eluent) to give the protected prostaglandin. This material is dissolved in 5 parts by volume of a 3:1:1 mixture of acetic acid; tetrahydrofuran; water and is allowed to stand at room temperature for 30–60 minutes. The solution is diluted with ether, washed with water five times, and dried over anhydrous sodium sulfate. The ether is removed by evaporation at reduced pressure and the residual oil is chromatographed on silica gel (60% ethyl acetate/hexane as eluent) to provide methyl 7-[3α-hydroxy-2β-4-hydroxy-4-methyl-6-cyclopropyl-1-trans-hexenyl)-5-oxocyclopentane]-1α-hept-4-cis-enoate having the following formula

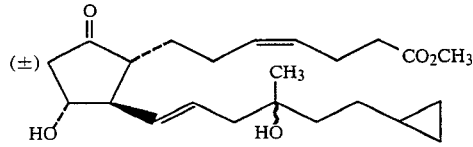

H' NMR data in CDCl₃
δ0.90 m, cyclopropane; δ1.17s, 16—CH₃;
δ3.66, s, methyl ester;
δ4.03 of C—11; δ5.34, m C—4,5

EXAMPLE 2

10 parts of 3-cyclopentyl propionic acid are dissolved in 150 parts by volume of ethyl ether and chilled to −20° C. under argon. 50 parts by volume of 2.8 molar methyl magnesium bromide are added dropwise. After the addition of the methyl magnesium bromide is completed, the mixture is allowed to warm to room temperature. The cloudy reaction mixture is treated with 1N hydrochloric acid and the clearified reaction mixture is extracted with ether followed by ethyl acetate. The combined organic extracts are washed with water and saturated sodium chloride solution, dried over anhydrous sodium sulfate, filtered and the solvent evaporated under reduced pressure. The residual oil is chromatographed on silica gel using 10% ethyl acetate/hexane as the eluent, to provide 4-cyclopentyl-2-butanone.

Following the procedure set out in Example 1 using equivalent quantities, 4-cyclopentyl-2-butanone is converted to methyl 7-[3α-hydroxy-2β-4-hydroxy-4-methyl-6-cyclopentyl-1-trans-hexenyl)-5-oxocyclopentane]-1α-hept-4-cis-enoate, having the formula

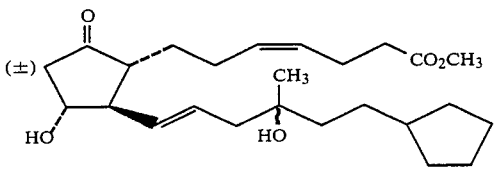

H' NMR data in CDCl$_3$
δ1.17s, 16—CH$_3$; δ3.66,s methyl ester; δ4.03q, C—11; δ5.34, m C—4,5

EXAMPLE 3

10 parts of cyclobutylcarboxylic acid chloride in tetrahydrofuran is hydrogenated over 10% palladium on carbon catalyst, to provide cyclobutylcarboxaldehyde. 25 parts of triphenylphosphoranylidene-2-propanone and 6.3 parts of the cyclobutylcarboxaldehyde in 60 parts by volume of benzene under nitrogen are refluxed for 8 hours. The solvent is removed by evaporation under reduced pressure to provide 4-cyclobutyl-3-buten-2-one.

7.5 parts of this material in ethanol is hydrogenated over 5% palladium on carbon to provide 4-cyclobutyl-2-butanone.

Following the procedures in Example 1 using equivalent quantities provides methyl 7-[3α-hydroxy-2β-4-hydroxy-4-methyl-6-cyclobutyl-1-trans-hexenyl)-5-oxocyclopentane]1α-hept-4-cis-enoate, having the following formula

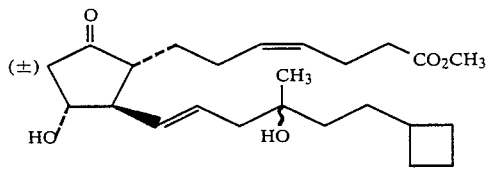

H' NMR data in CDCl$_3$
δ1.16s, 16—CH$_3$; δ3.65,s methyl ester; δ4.03, q, C—11
δ5.32,m C—4,5

EXAMPLE 4

1.0 Part of the trans-vinylstannane product of Example 1 is dissolved in 3.0 parts by volume of dry tetrahydrofuran, cooled to −60° C. and treated with 0.87 parts by volume of 2.3 molar n-butyl lithium. The reaction is stirred for one hour at −60° C. and then treated with an ether solution containing 0.26 parts of copper 1-pentynilide and 0.64 parts of hexamethylphosphorous triamide. The solution is then stirred for an additional 10 minutes at −60° C. and an ether solution containing 0.35 parts of the (±) methyl 7-(3-triethylsilyloxy-5-oxocyclopent-1-ene)-hept-4-cis-enoate is added. The solution is stirred for one hour and then treated with 0.3 parts of t-butyldimethylsilyl chloride in 2 parts by volume of ether, followed by the addition of 3 parts by volume of hexamethyl phosphoric triamide. The mixture is stirred at −20° C. for 30 minutes and then allowed to come slowly up to 0° C. The mixture is then poured into ether and 1N hydrochloric acid. The layers are separated and the ether layer is washed with water dried over sodium sulfate and stripped of solvent. The residue is chromatographed on silica gel (5% ethyl acetate, 95% hexane) to give racemic methyl[7-3-triethylsilyloxy-2β-(4-trimethylsilyloxy-4-methyl-6-cyclopropyl-1-trans-hexenyl)-5-t-butyldimethylsilyloxy-cyclopent-1(5)-ene]-1α-hept-4-cis-enoate. 0.7 Parts of the above compound in 10 parts tetrahydrofuran is cooled to 0° and treated with 0.038 parts of lithium aluminum hydride. After 1 hour at 0°, the reaction mixture was quenched with water. The solution is diluted with ether, washed with water, dried over sodium sulfate and evaporated to dryness under reduced pressure. The residue is taken up in 25 parts by volume of a 3:1:1 mixture of acetic acid, water and tetrahydrofuren and allowed to stand at room temperature for 16 hours. The solution is diluted with ether, washed with water 4–5 times, dried over sodium sulfate and evaporated to dryness. The residue is chromatographed on silica gel (10% ethyl acetate as eluent) to give as a colorless viscous oil the product 7-[3α-hydroxy-2β-4-hydroxy-4-methyl-6-cyclopropyl-1-trans-hexenyl)-5-oxocyclopentane]-1α-hept-4-cis-en-1-ol having the formula:

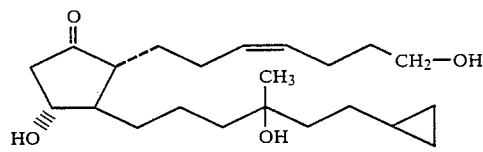

EXAMPLE 5

Following the procedures set out in Example 1, using equivalent quantities, 8-(3-triethylsilyloxy-5-oxocyclopent-1-ene)-1-triethylsilyloxy-2-oxo-oct-5-cis-ene. (U.S. Pat. No. 4,322,543) and 4-cyclopentyl-2-butanone are converted to 8-[3α-hydroxy-2β-4-hydroxy-4-methyl-6-cyclopentyl-1-trans-hexenyl)5-oxocyclopentene]-1α-1-hydroxy-2-oxo-oct-5-cis-ene having the formula:

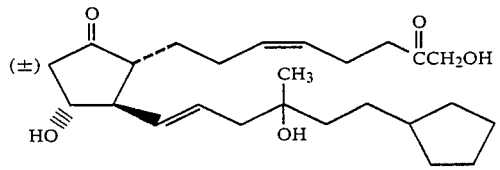

What is claimed is:
1. A Compound of the formula

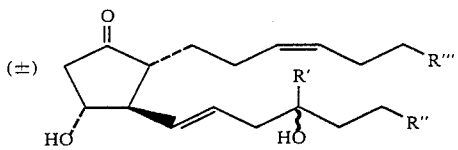

wherein R''' represents hydroxymethyl, hydroxyacetyl, or —CO$_2$R'''' wherein R'''' represents hydrogen or lower alkyl containing 1-6 carbon atoms;

R' represents lower alkyl containing 1 to 6 carbon atoms, vinyl or ethynyl;

R'' represents cycloalkyl containing 3 to 5 carbon atoms; and the wavy line represents optional R,S stereochemistry 2. A compound according to claim 1 which is methyl 7-[3α-hydroxy-2β-4-hydroxy-4-methyl-6-cyclopropyl-1-transhexenyl)-5-oxocyclopentane]-1α-hept-4-cis-enoate.

3. A compound according to claim 1 which is methyl 7-[3α-hydroxy-2β-4-hydroxy-4-methyl-6-cyclobutyl-1-trans-hexenyl)-5-oxocyclopentane]-1α-hept-4-cis-enoate.

4. A compound according to claim 1 which is methyl 7-[3α-hydroxy-2β-4-hydroxy-4-methyl-6-cyclopentyl-1-trans-hexenyl)-5-oxocyclopentane]-1α-hept-4-cis-enoate.

5. A compound according to claim 1 which is 8-[3α-(hydroxy-2β-4-hydroxy-4-methyl-6-cyclopentyl-1-trans-hexenyl)5-oxocyclopentane]1-α-1-hydroxy-2-oxo-oct-5-cis-ene.

6. A compound according to claim 1 which is 7-[3α-hydroxy-2β-4-hydroxy-4-methyl-6-cyclopropylhexenyl)-5-oxocyclopentane]-1α-hept-4-cis-en-1-ol.

* * * * *